US00PP15856P2

(12) United States Plant Patent
Schräder

(10) Patent No.: US PP15,856 P2
(45) Date of Patent: Jul. 12, 2005

(54) ***CONVOLVULUS* PLANT NAMED 'SUMCOV 01'**

(50) Latin Name: *Convolvulus sabatius*
Varietal Denomination: Sumcov 01

(76) Inventor: Ralf Schräder, Ahornweg 6a, D-59348 Lüdinghausen (DE)

( * ) Notice: Subject to any disclaimer, the term of this patent is extended or adjusted under 35 U.S.C. 154(b) by 0 days.

(21) Appl. No.: 10/759,607

(22) Filed: Jan. 16, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Convolvulus* plant named 'Sumcov 01', characterized by its trailing plant habit; freely flowering habit; vigorous plant growth habit; and single white-colored flowers.

2 Drawing Sheets

Botanical classification/cultivar designation: *Convolvulus sabatius* cultivar Sumcov 01.

BACKGROUND OF THE INVENTION

The present Invention relates to a new and distinct cultivar of *Convolvulus* plant, botanically known as *Convolvulus sabatius,* and hereinafter referred to by the name 'Sumcov 01'.

The new *Convolvulus* is a product of a planned breeding program conducted by the Inventor in Lüdinghausen, Germany. The new *Convolvulus* originated from a cross-pollination made by the Inventor of two unnamed selections of *Convolvulus sabatius,* not patented. The new *Convolvulus* was selected by the Inventor in 2002 in a controlled environment in Lüdinghausen, Germany.

Asexual reproduction of the new cultivar by terminal cuttings in Lüdinghausen, Germany since 2002, has shown that the unique features of this new *Convolvulus* are stable and reproduced true to type in successive generations.

SUMMARY OF THE INVENTION

Plants of the cultivar Sumcov 01 have not been observed under all possible environmental conditions. The phenotype may vary somewhat with variations in environment such as temperature and light intensity without, however, any variance in genotype.

The following traits have been repeatedly observed and are determined to be the unique characteristics of 'Sumcov 01'. These characteristics in combination distinguish 'Sumcov 01' as a new and distinct *Convolvulus* cultivar:

1. Outwardly spreading and trailing plant habit.
2. Freely flowering habit.
3. Vigorous plant growth habit.
4. Single white-colored flowers.

Plants of the new *Convolvulus* are more outwardly spreading and differ in flower color when compared to plants of the parent selections.

Plants of the cultivar Sumcov 01 can be compared to plants of the *Convolvulus* cultivar Compact, not patented. However, in side-by-side comparisons conducted in Lüdinghausen, Germany, plants of the new *Convolvulus* and the cultivar Compact differed in the following characteristics:

1. Plants of the new *Convolvulus* were more outwardly spreading than plants of the cultivar Compact.
2. Plants of the new *Convolvulus* were more freely flowering than plants of the cultivar Compact.
3. Plants of the new *Convolvulus* had larger flowers than plants of the cultivar Compact.
4. Flowers of the new *Convolvulus* and the cultivar Compact differed in flower coloration as plants of the cultivar Compact had violet-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the following detailed botanical description which accurately describe the colors of the new *Convolvulus.*

The photograph on the first sheet comprises a side perspective view of a typical plant of 'Sumcov 01' grown in a container.

The photograph on the second sheet is a close-up view of a typical flower and leaves of 'Sumcov 01'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following botanical description were grown in 21-cm containers during the spring, summer and fall for 26 weeks in a controlled outdoor environment in Lüdinghausen, Germany. During the production of the plants, day temperatures were about 16 to 20° C., night temperatures were about 10 to 16° C. and light levels were about 15,000 to 25,000 lux.

Botanical classification: *Convolvulus sabatius* cultivar Sumcov 01.

Parentage:

*Female parent.*—Unnamed *Convolvulus sabatius* selection, not patented.

*Male parent.*—Unnamed *Convolvulus sabatius* selection, not patented.

Propagation:

*Type cutting.*—Terminal vegetative cuttings.

*Time to initiate roots, summer.*—About 10 days at 18° C.

*Time to initiate roots, winter.*—About 12 days at 18° C.

*Time to develop roots, summer.*—About 24 days at 16° C.

*Time to develop roots, winter.*—About 26 days at 16° C.

*Root description.*—Fine and well-branched.

Plant description:

*Form.*—Annual flowering plant; outwardly spreading to trailing. Freely branching, about 10 to 15 lateral branches per plant. Vigorous plant growth habit.

*Usage.*—Appropriate for hanging baskets, window boxes and patio containers.

*Plant height* (*from soil level to top of plant plane*).—About 20 to 25 cm.

*Plant diameter.*—About 40 to 50 cm.

*Stem description.*—Main branches, length: About 70 to 80 cm. Main branches, diameter: About 4 mm. Lateral branches, length: About 60 to 70 cm. Lateral branches, diameter: About 1.5 mm. Internode length: About 3 to 3.5 cm. Texture: Smooth. Color: 143B.

*Foliage description.*—Arrangement: Alternate; simple. Length: About 2.8 to 3 cm. Width: About 1.8 to 2 cm. Shape: Cordate, rotund. Apex: Rounded. Base: Cordate. Margin: Entire. Aspect: Flat. Texture, upper and lower surfaces: Slightly pubescent. Venation pattern: Pinnate. Color: Developing and fully expanded foliage, upper surface: 136A. Developing and fully expanded foliage, lower surface: 137C. Venation, upper and lower surfaces: 144A. Petiole length: About 7 mm. Petiole diameter: About 1 mm. Petiole color: 144A.

Flower description:

*Flower type and habit.*—Single salverform flowers, axillary; flowers face upward and outward. Freely flowering habit with about 80 to 100 flowers and buds per plant.

*Natural flowering season.*—Flowering from April until frost in the autumn in Germany; flowering continuous during this period.

*Fragrance.*—None detected.

*Flower longevity on the plant.*—About two days, flowers not persistent.

*Flower size.*—Diameter: About 3 cm. Depth (height): About 1 mm.

*Flower buds.*—Length: About 8 mm. Diameter: About 2 mm. Shape: Conical. Color: N155A.

*Petals.*—Arrangement/appearance: Single whorls of five petals, fused, flowers salverform. Length: About 1.4 cm. Width: About 1.2 cm. Shape: Roughly oblanceolate. Apex: Obtuse. Margin: Entire. Texture, upper and lower surfaces: Smooth, glabrous. Color: When opening, upper and lower surfaces: Close to N155A. Fully opened, upper and lower surfaces: Close to N155A.

*Sepals.*—Arrangement/appearance: Single whorl of five sepals, fused at base; star-shaped. Length: About 5 mm. Width: About 2 mm. Shape: Roughly ovate. Apex: Acuminate. Base: Truncate. Margin: Entire. Color, upper surface: 144A. Color, lower surface: 144B.

*Peduncles.*—Length: About 2.5 cm. Width: About 1 mm. Strength: Flexible. Texture: Smooth. Color: 138A.

*Reproductive organs.*—Stamens: Quantity: About four per flower. Anther shape: Oblong. Anther length: About 1 mm. Anther color: 155B. Pollen amount: Moderate. Pollen color: 155B. Pistils: Quantity: One per flower. Pistil length: About 0.5 mm. Stigma shape: Filiform. Stigma color: 155B. Style length: About 3 mm. Style color: 155B. Ovary color: 18B. Seed: Quantity: Inconsistent seed production, flowers typical sterile. Seed length: About 0.3 mm. Seed diameter: About 0.3 mm. Seed color: 178B.

Disease/pest resistance: Plants of the new *Convolvulus* have not been noted to be resistant to pathogens or pests common to *Convolvulus*.

Temperature tolerance: Plants of the new *Convolvulus* have been observed to be tolerant to temperatures from 0 to 40° C.

It is claimed:

1. A new and distinct cultivar of *Convolvulus* plant named 'Sumcov 01', as illustrated and described.

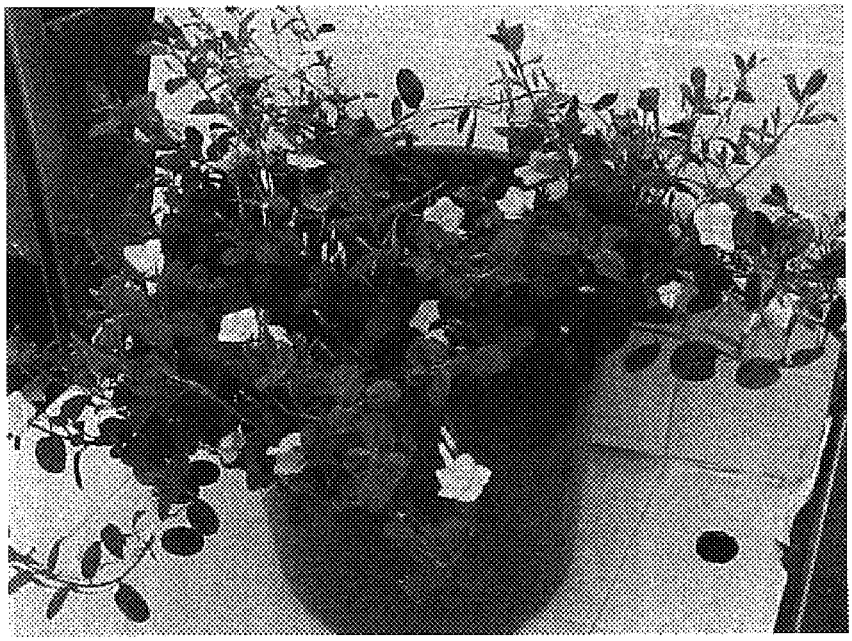

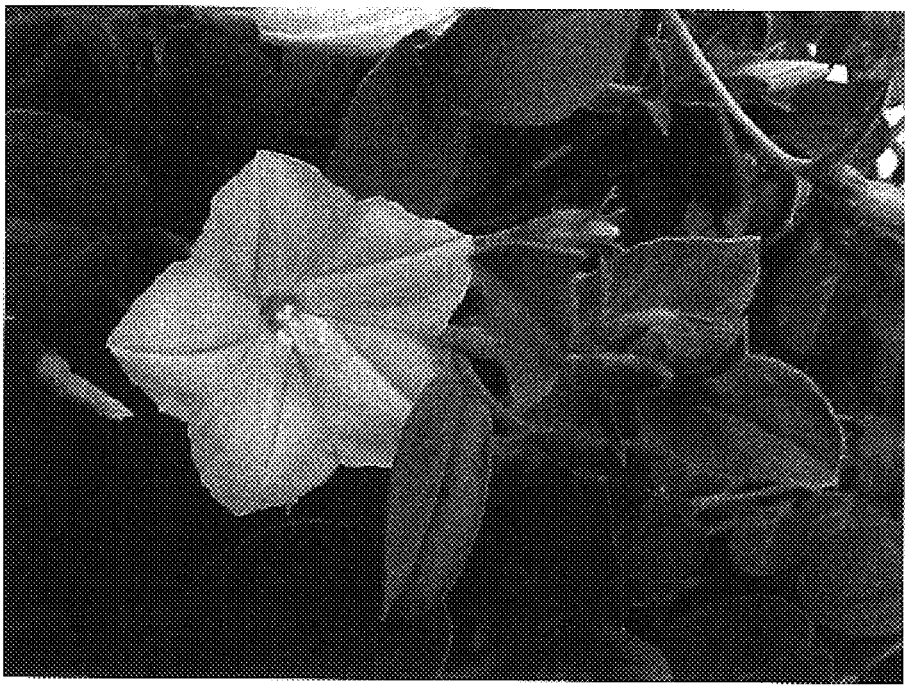

* * * * *